United States Patent [19]
Wu et al.

[11] Patent Number: 6,010,882
[45] Date of Patent: Jan. 4, 2000

[54] PRODUCTION OF BIOLOGICALLY ACTIVE RECOMBINANT INSULIN-LIKE GROWTH FACTOR II POLYPEPTIDES

[75] Inventors: Jen-Leih Wu; Jyh-Yih Chen; Chi-Yao Chang, all of Taipei, Taiwan

[73] Assignee: Academia Sinica, Taipei, Taiwan

[21] Appl. No.: 09/003,708

[22] Filed: Jan. 7, 1998

Related U.S. Application Data

[60] Provisional application No. 60/034,736, Jan. 10, 1997.

[51] Int. Cl.[7] ............................ C12N 15/18; C12N 15/63; C12N 5/00; C07K 14/65
[52] U.S. Cl. ........................ 435/69.4; 435/69.1; 435/325; 435/243; 435/320.1; 536/23.1; 536/23.51; 530/399
[58] Field of Search .................................. 435/69.1, 69.4, 435/71.1, 325, 243, 252.33; 536/23.1, 23.51

[56] References Cited

U.S. PATENT DOCUMENTS 5,476,779  12/1995  Chen et al. ............................ 435/240.1

OTHER PUBLICATIONS

Rentui–Delrue et al. DNA 8(4):261–270, 1989.
Rentui–Delrue et al. DNA 8(4):271–278, 1989.
DNA and Cell Biology, J.Y. Chen et al., Production of Biologically Active Recombinant Tilapia Insulin–Like Growth Factor–II Polypeptides in *Escherichia coli* Cell and Characterization of the Genomic Structure of the Coding Region, 16:–883–892 (T) 1997.
DNA, Alane Gray et al., Tissue–Specific and Developmentally Regulated Transcription of the Insulin–Like Growth Factor 2 Gene, vol. 6, No. 4, 1987.
Histochemistry, Reinecke et al., IGF–2–like peptides are present in insulin cells of the elasmobranchian endocrine pancreas: an immunohistochemical and chromatographic study, 102:365–371 (1994).
Proc. Natl. Acad. Sci. USA, Michael Shamblott, Identification of a second insulin–like growth factor in a fish species, 89:8913–8917 1992.
DNA and Cell Biology, Vadim Kavsan, Structure of the Chum Salmon Insulin–Like Growth Factor I Gene, 12:729–737 1993.

*Primary Examiner*—John Ulm
*Assistant Examiner*—Christine Saoud
*Attorney, Agent, or Firm*—Fei-Fei Chao; Snider & Chao, LLP

[57] ABSTRACT

The present invention relates to the finding and construction of fish insulin-like growth factor II (IGF-II) cDNAs which can be cloned and expressed in cells. This invention also relates to the production of biologically active fish IGF-II polypeptides by a gene expression system using fish IGF-II cDNAs. The fish IGF-II cDNAs have 1977 bp which transcribe into a prepeptide (signal peptide), and B, C, A, D, E domain peptides. The fish mature IGF-II is a single polypeptide containing the $NH_2$-B-C-A-D-COOH domains. The mature IGF-II polypeptide is 7 kDa in weight and has 70 amino acids. The fish recombinant IGF-II CDNA can be cloned and expressed in *E. coli*, yeast, baculovirus, and fish cells.

17 Claims, 7 Drawing Sheets

```
  1   gaattcgcggccgcctaactcacctgcaatcacaccaacaataattcccaacatttg
                                  *
 61   actactgccatctgacatggaaacccagcaaagatacggacatcactcactttgccacac
                         M  E  T  Q  Q  R  Y  G  H  H  S  L  C  H  T
121   ctgccggagaacgcagaacagcagaatgaaggtccagagatgtcttcgacgagtcgggc
       C  R  R  T  Q  N  S  R  M  K  V  Q  R  M  S  S  T  S  R  A
181   gctgctctttgcactggccctgacgctctacgtagtggaaatggcctcggcggagacgct
       L  L  F  A  L  T  L  Y  V  V  E  M  A  S  A  E  T  L
241   gtgtggggagaactggtggatgcgctgcagtttgtctgtgaagacagaggctttatt
       C  G  G  E  L  V  D  A  L  Q  F  V  C  E  D  R  G  F  Y  F
301   cagtaggccaaccagcaggggtaacaaccgacgCCcccagacccgtgggatcgtagagga
       S  R  P  T  S  R  G  N  N  R  R  P  Q  T  R  G  I  V  E  E
361   gtgttgtttccgtagctgtgacctcaactgtgccaacctgccaa
       C  C  F  R  S  C  D  L  N  L  L  E  Q  Y  C  A  K  P  A  K
421   gtccgaaagggacgtgtcagcacctctctacaggtcataccggtgatgcccgcactaaa
       S  E  R  D  V  S  A  T  S  L  Q  V  I  P  V  M  P  A  L  K
```

FIG.1A

```
481   acaggaagttccgaagaagcaacatgtgaccgtgaagtattccaaatacgaggtgtggca
       Q  E  V  P  K  K  Q  H  V  T  V  K  Y  S  K  Y  E  V  W  Q 541   gaggaaggcgcggccagcgcggctccggagggtgtcccgccattctgagggccagaaagta
       R  K  A  A  Q  R  L  R  R  G  V  P  A  I  L  R  A  R  K  Y 601   taagaggcacgcggagagattaaagccaaggagcaggctatcttccagcccctgat
       K  R  H  A  E  K  I  K  A  K  E  Q  A  I  F  H  R  P  L  I 661   cagccttcctagcaagctgcctcccgtgttactcaccacggacaactttgtcagtcacaa
       S  L  P  S  K  L  P  P  V  L  L  T  T  D  N  F  V  S  H  K
                                                                    #

721   atgagcccgctgccagcccttgcacagacaagagtttgagggtgaaaaagactagg 781   ggattatagctttgtctctgacgtcattcagtggcagtcctctttgacctccccctgccc
841   tgtccgagctcgagtccaatccctgcacatatccactacgtcttgaacccctggccc
901   ttttctaatgacccnntaaaacccgaactccccccaccactcctctcctcctctcctgg
961   cacacagacatgcctcacattcttcctgtcctgaactcttctctccactctctttcag
1021  tcactgatacaaaaggcacaaacacaaaaagtcgaacaaaaagttaacaatttggctgaa
1081  tgcggttcagtggatcctttaagcaagacaaagagaaggaaaaagaagatgaaag
1141  agatctgtcgtttgcaagtgtcaagagcgctgcatgaaagaatccattccacctcattttcctga
1201  agacaactgaaagtgaagagctgcttgcatgaaagaatccattccacctcattttcctga
1261  ggcaaaagaaatctctgttagtttgcacctctacctgtaatgggacttcca
1321  cactgtaaggaattatttgtaaattagattcctgttccagcaccttgatcacaaac
```

FIG.1B

```
1381  aaaaagcagaaaagagtctgcaaaattgcacattgccacggattacgtctttgtaagaaa
1441  aaaatgggcactatttttttatgaacaatgaacgtgtagcttaaaaaatgtcatggtgc
1501  tagctttgggaatggactcaaagagagagtggaaaagcacgtttttttcttttgaatta
1561  ataattaaagctttccgttttaaggaaagtgtgacttttaaaaaaggaaaattttgga
1621  tatggggagctctggcagtggcaatgtcaaggggaaagagtcactgaggaaaatatg
1681  ggctgtgttggcatctaggctcatggtgagtnctagcggctgctatttactagtttgcca
1741  gcataagncagcaagggatgaccgagacccgagtccctgttcctccctgtccctctgaggc
1801  tgctggacacatggagcactatggggacactacacatgggacaccatggccacctggattgg
1861  gacagtactatagttcggggacagtacaacctgtttgccatggctttgcgactgttctg
1921  gcaggaagtaacatggactaagaacgagtggggcggccgcgaattc
```

FIG.1C

|  | B domain | C domain | A domain | D domain |
|---|---|---|---|---|
| Tilapia | EMAS..AETLCGGELVDALQFVCEDRGFYFSRPT | SRGNNRRPQTR | GIVEECCFRSCDLNLLEQYCA | KPAKSE |
| Sparus aurata | EVAS..AETLCGGELVDALQFVCEDRGFYFSRPT | SRGNNRRPQNR | GIVEECCFRSCDLNLLEQYCA | KPAKSE |
| Rainbow trout | EVAS..AETLCGGELVDALQFVCEDRGFYFSRPT | SRSNSRRSQNR | GIVEECCFRSCDLNLLEQYCA | KPAKSE |
| Chicken | AYGTAETLCGGELVDTLQFVCGDRGFYFSPRV | GRNN.RR.INR | GIVEECCFRSCDLALLETYCA | KSVKSE |
| Human | AYRPSETLCGGELVDTLQFVCGDRGFYFSRPA | SRVS.RR..SR | GIVEECCFRSCDLALLETYCA | TPAKSE |
| Rat | AYRPSETLCGGELVDTLQFVCGDRGFYFSRPS | SRAN.RR..SR | GIVEECCFRSCDLALLETYCA | TPAKSE |
| Mouse | AYGPGETLCGGELVDTLQFVCSDRGFYFSRPS | SRAN.RR..SR | GIVEECCFRSCDLALLETYCA | TPAKSE |
| Sheep | AYRPSETLCGGELVDTLQFVCGDRGFYFSRPS | SRIN.RR..SR | GIVEECCFRSCDLALLETYCA | APAKSE |
| Ancestral vertebrate | ??A?????ETLCGGELVD?LQFVC?DRGFYFSR?? | ?R???RR???R | GIVEECCFRSCDL?LLE?YCA | ???KSE | signal peptide

Tilapia          METQQRYGHHSLCHTCRRTQNSRMKVQRMSSTSRALLFALALTLYV
Sparus aurata    METQQRHGRHSLCHTCRRTESSRMKVKKMSSSSRALLFALALTLYV
Rainbow trout    METQKRHEYHSVCHTCRRTENTRMKVKMMSSSSNRVLVIALALTLYIV
Chicken                          MCAARQILLLLAFLAYALDSAA
Human                            MGIPWGKSMLVLLTFLAFASCCIA
Rat                              MGIPVGKSMLVLLISLAFALCCIA
Mouse                            MGIPVGKSMLVLLISLAFALCCIA
Sheep                            MGITAGKSMLALLAFLAFASCCYA

FIG.2A

E domain
Tilapia        RDVSATSLQVIPVMPALKQEVPKKQHVTVKYSKYEVWQRKAAQRLRRGVPAILRARKYKRHAEKIKAKEQA.IFHRPLI
Sparus aurata  RDVSATSTQVLPVMPPLKQEVSRKQHVTVKYSKYEVWQRKAAQRLRRGVPAILRAKKYRRQAEKIKAQEQA.IFHRPLI
Rainbow trout  RDVSATSLQIIPMVPTIKQDVPRK.HVTVKYSKYEAWQRKAAQRLRRGVPAILRARKFRRQAVKIKAQEQA.MFHRPLI
Chicken        RDLSATSLAGLPALN..KESFQKPSH..AKYSKYNVWQKKSSQRLQREVPGILRARRYRWQAEGLQAAEEARAMHRPLI
Human          RDVS.TPPTVLP......DNFRR..YPVGKFFQYDTW.KQSTQRLRRGLPALLRARRGHVLAKELEAFREAKR.HRPLI
Rat            RDVS.TSQAVLP......DDFPR..YPVGKFKFDTW.RQSAGRLRRGLPALLRARRGRMLAKELEAFREAKR.HRPLI
Mouse          RDVS.TSQAVLP......DDFPR..YPVGKFFQYDTW.RQSAGRLRRGLPALLRARRGRMLAKELKEFREAKR.HRPLI
Sheep          RDVS.ASTTVLP......DDFTA..YPVGKFFQSDTW.KQSTQRLRRGLPAFLRARRGRTLAKELEALREAKS.HRPLI Tilapia        SLPSKLPPVLLTTDNFVSHK*..
Sparus aurata  SLGSKLPPVLLATDNYVNHK*..
Rainbow trout  TLPSKLPPVLPPTDNYVSHN*..
Chicken        SLPSQRPPAPRASPEATGPQE*.
Human          ALPTQDPA.HGGAPPEMASNRK*
Rat            VLPPKDPA.HGGASSEMSSNHQ*
Mouse          VLPPKDPA.HGGASSEMSSNHQ*
Sheep          ALPTQDPATHGGASSEASSD*..

FIG.2B

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 210 base pairs
        (B) TYPE: nucleic acid
        (C) STRANDEDNESS: BOTH (D) TOPOLOGY: BOTH (ii) MOLECULE TYPE:    molecular basis (iii) HYPOTHETICAL: No (xi) SEQUENCE DESCRIPTION:  SEQ ID NO:1:

GAAATGGCCT CGGCGGAGAC GCTGTGTGGG GGAGAACTGG TGGATGCGCT GCAGTTTGTC    60

TGTGAAGACA GAGGCTTTTA TTTCAGTAGG CCAACCAGCA GGGGTAACAA CCGACGCCCC   120

CAGACCCGTG GGATCGTAGA GAGTGTTGTT TCCGTAGCTG TGACCTCAAC CTACTGGAGC   180

AGTACTGTGC AAACCTGCCA AGTCCGAAAG                                    210

(2) INFORMATION FOR SEQ ID NO:2:

(i) SEQUENCE CHARACTERISTICS:
            (A) LENGTH:    141 base pairs
            (B) TYPE:      nucleic acid
            (C) STRANDEDNESS: BOTH
            (D) TOPOLOGY: BOTH (ii) MOLECULE TYPE:    molecular basis (iii) HYPOTHETICAL: No (xi) SEQUENCE DESCRIPTION:  SEQ ID NO:2:

ATGGAAACCC AGCAAAGATA CGGACATCAC TCACTTTGCC ACCACTGCCG GAGAACGCAG    60

AACAGCAGAA TGAAGGTCCA GAGGATGTCT TCGACGAGTC GGGCGCTGCT CTTTGCACTG   120

GCCCTGACGC TCTACGTAGT G                                             141

(2) INFORMATION FOR SEQ ID NO:3:

(i) SEQUENCE CHARACTERISTICS:
            (A) LENGTH:    294 base pairs
            (B) TYPE:      nucleic acid
            (C) STRANDEDNESS: BOTH
            (D) TOPOLOGY: BOTH (ii) MOLECULE TYPE:    molecular basis (iii) HYPOTHETICAL: No (xi) SEQUENCE DESCRIPTION:  SEQ ID NO:3:

AGGGACGTGT CAGCCACCTC TCTACAGGTC ATACCGGTGA TGCCCGCACT AAAACAGGAA    60

GTTCCGAAGA AGCAACATGT GACCGTGAAG TATTCCAAAT ACGAGGTGTG GCAGAGGAAG   120

GCGGCCCAGC GGCTCCGGAG GGGTGTCCCC GCCATTCTGA GGGCCAGAAA GTATAAGAGG   180

CACGCGGAGA AGATTAAAGC CAAGGAGCAG GCTATCTTCC ACAGGCCCCT GATCAGCCTT   240

CCTAGCAAGC TGCCTCCCGT GTTACTCACC ACGGACAACT TTGTCAGTCA CAAA         294

(2) INFORMATION FOR SEQ ID NO:4:

(i) SEQUENCE CHARACTERISTICS:
            (A) LENGTH:    70 amino acids
            (B) TYPE:      amino acid
            (D) TOPOLOGY: Unknown (ii) MOLECULE TYPE:    polypeptide (iii) HYPOTHETICAL: No (xi) SEQUENCE DESCRIPTION:  SEQ ID NO:4:

Glu Met Ala Ser Ala Glu Thr Leu Cys Gly Gly Glu Leu Val Asp Ala
1               5                   10                  15

Leu Gln Phe Val Cys Glu Asp Arg Gly Phe Tyr Phe Ser Arg Pro Thr

-continued

```
                  20                  25                  30
Ser Arg Gly Asn Asn Arg Arg Pro Gln Thr Arg Gly Ile Val Glu Glu
            35                  40                  45

Cys Cys Phe Arg Ser Cys Asp Leu Asn Leu Leu Glu Gln Tyr Cys Ala
        50                  55                  60

Lys Pro Ala Lys Ser Glu
65                  70

(2) INFORMATION FOR SEQ ID NO:5:

(i) SEQUENCE CHARACTERISTICS:
        (A) LENGTH:    47 amino acids
        (B) TYPE:      amino acid
        (D) TOPOLOGY:  Unknown (ii) MOLECULE TYPE:     polypeptide (iii) HYPOTHETICAL:  No (xi) SEQUENCE DESCRIPTION:  SEQ ID NO:5:

Met Glu Thr Gln Gln Arg Tyr Gly His His Ser Leu Cys His Thr Cys
1               5                   10                  15

Arg Arg Thr Gln Asn Ser Arg Met Lys Val Gln Arg Met Ser Ser Thr
                20                  25                  30

Ser Arg Ala Leu Leu Phe Ala Leu Ala Leu Thr Leu Tyr Val Val
            35                  40                  45

(2) INFORMATION FOR SEQ ID NO:6:

(i) SEQUENCE CHARACTERISTICS:
        (A) LENGTH:    98 amino acids
        (B) TYPE:      amino acid
        (D) TOPOLOGY:  Unknown (ii) MOLECULE TYPE:     polypeptide (iii) HYPOTHETICAL:  No (xi) SEQUENCE DESCRIPTION:  SEQ ID NO:6:

Arg Asp Val Ser Ala Thr Ser Leu Gln Val Ile Pro Val Met Pro Ala
1               5                   10                  15

Leu Lys Gln Glu Val Pro Lys Lys Gln His Val Thr Val Lys Tyr Ser
                20                  25                  30

Lys Tyr Gln Val Trp Gln Arg Lys Ala Ala Gln Arg Leu Arg Arg Gly
            35                  40                  45

Val Pro Ala Ile Leu Arg Ala Arg Lys Tyr Lys Arg His Ala Glu Lys
        50                  55                  60

Ile Lys Ala Lys Glu Gln Ala Ile Phe His Arg Pro Leu Ile Ser Leu
65                  70                  75                  80

Pro Ser Lys Leu Pro Pro Val Leu Leu Thr Thr Asp Asn Phe Val Ser
                85                  90                  95

His Lys
```

PRODUCTION OF BIOLOGICALLY ACTIVE RECOMBINANT INSULIN-LIKE GROWTH FACTOR II POLYPEPTIDES

RELATED APPLICATION

This application claims the priority of the U.S. Provisional Patent Application No. 60/034,736, filed on Jan. 10, 1997. The content of said Provisional Patent Application is herein incorporated by reference.

FIELD OF THE INVENTION

This invention (published in *DNA and Cell Biology* (1997), 16:883–892, hereinafter incorporated by reference) relates to a fish insulin-like growth factor II (IGF-II) cDNA and the biologically active IGF-II polypeptide expressed by said cDNA, and more particularly, relates to a recombinant tilapia IGF-II cDNA and the expression of said recombinant IGF-II cDNAs in cells. This recombinant IGF-II cDNA can be cloned and expressed in *E. coli*, yeast, baculovirus, and fish cells.

BACKGROUND OF THE INVENTION

Insulin-like growth factors (IGFs) are mitogenic peptide hormones that play important roles in the growth and differentiation of vertebrates. IGFs are translated as a prepropeptide, which can be divided into an N-terminal prepeptide (which is also called a signal or leader peptide), a B to D domain polypeptide (which contains peptides from B, C, A and D domains), and a C-terminal E-domain peptide (which is also called a trailer peptide). The IGF signal and E peptides are proteolytically removed from the B to D polypeptide during protein maturation (Shamblott and Chen (1992), *Proc. Natl. Acad. Sci.* USA, 89:8913–8917). For this reason, the B to D domain polypeptide is also called "the IGF mature peptide".

So far, the functions of the IGF signal and E peptides are unknown. However, it is well known in the art that a signal peptide may facilitate the transport of protein out of the cell membrane. As for the E peptide, since the E peptide is a part of the IGF preproprotein and may actually be secreted as a part of an intact prohormone, it is possible that the E peptide may affect the processing, transport, or secretion of the mature peptide. It is also possible that the E peptide may indirectly or directly modulate the degradation, receptor interaction, or binding protein interactions of the mature peptide.

There are two kinds of IGFs, namely, IGF-I and IGF-II. IGF-I and IGF-II share high homology of protein folding structure and similar growth promotion effects, even though they are mediated by different IGF receptors (i.e., IGF-I is mediated by a tyrosine kinase receptor, whereas IGF-II is mediated by a mannose-6-phosphate receptor). IGF-I is a 70 amino acid polypeptide which mediates the growth-promoting actions of growth hormone as well as having important local paracrine and autocrine roles in multiple organs (Kavsan et al. (1993), *DNA and Cell Biology*, 12:729–737).

In mammals, the mature form of IGF-II is a neutral protein consisting of 67 amino acid residues with three disulfide bonds. IGF-II is a single-chain polypeptide that contains a $NH_2$-B-C-A-D-COOH domain. The signal peptide and E domain are removed in mature peptide. The cDNA sequences of IGF-II have been reported highly conserved in different mammals, including chickens, sheep, mice, humans, and rats. The mammalian IGF-II is primarily produced in liver during prenatal development under the control of placental lactogen (Gray et al. (1987), *DNA*, 6:283–295). Because of its role as a key component regulating fetal growth, IGF-II is also called a "fetal growth factor".

IGF-II has a complex gene structure. In humans, IGF-II gene consists of 10 exons and spans about 30 kb of DNA. The DNA sequence encoding the mature IGF-II polypeptides in humans is contained within exons 8, 9, and 10. In rat and mouse, IGF-II genes consist of 6 exons and span about 12 kb of DNA and the DNA sequence encoding the prepropeptide of rat or mouse IGF-II is contained within exons 4, 5, and 6.

Up until now, the gene structure and protein function of IGF-II in fish have remained unidentified. IGF-II like peptides have been reported present in the insulin cells of the elasmobranchian endocrine pancreas of fish (Reinneke et al. (1994), *Histochemistry*, 102:365–371). However, whether IGF-II is functioned as autocrine or paracrine is so far unclear. In addition, although so far two IGF-II cDNAs have been discovered in the liver of two fish species: *Sparus aurata* (Duguay et al. (1996), *J. Mol. Endocrinol.*, 16:123–132) and rainbow trout (Shamblott and Chen (1993), supra), there has been no report or study relating to the expression of fish IGF-II in cells as well as the physiological activity of fish IGF-II in vivo. Furthermore, there has been no report with regard to the findings of IGF-II cDNA in tilapia (*Oreochromis mossambicus*), and the production of a biologically active IGF-II polypeptide from a tilapia cDNA.

The invention to be presented below describes the cloning and sequencing of a fish IGF-II gene and the production of the biologically active fish IGF-II recombinant polypeptides. The establishment of a gene expression system is important because it provides a multifaceted channel for studies of the functional activity of the expressed proteins. In this case, the successful development of a gene expression system for fish IGF-II is especially important because it not only allows for the production of high quality fish IGF-II protein which facilitates the antibody production for immunohistochemical study (e.g., RIA, ELISA, etc.), but also provides large quantities of fish IGF-II protein for studies of the physiological functions of IGF-II in fish, particularly in determining the stimulatory effects on growth of juvenile fish.

SUMMARY OF THE INVENTION

The present invention describes (1) the identification of the complete coding region of a fish genomic IGF-II in a cDNA library, (2) the sequence analysis of a fish IGF-II cDNA, (3) the construction of a recombinant fish IGF-II expression vector, (4) the expression of fish recombinant IGF-II protein in *Escherichia coli* (*E. coli*), yeast, baculovirus, and fish cells, and (5) the biological function of the fish recombinant IGF-II protein.

The tilapia DNA molecule which encodes an IGF-II mature polypeptide comprises a B-D domain DNA molecule having the nucleic acid sequence of SEQ ID NO:1. An S domain DNA molecule (SEQ ID NO:2) and/or an E domain DNA molecule (SEQ ID NO:3) can be added to the B-D domain DNA molecule to construct an expression vector.

BRIEF DESCRIPTION OF THE DRAWINGS

FIG. 1 shows the nucleotide sequence of tilapia (hybrid) IGF-II cDNA and the predicted amino acid sequence of the hormone. The nucleotides are numbered beginning with the first nucleotide at the 5' end. The number on the second line indicates the order of the amino acid position. Asterisk (*), start codon; #, stop codon; n, uncertain cDNA codon.

FIG. 2 is a comparison of the amino acid sequences of tilapia IGF-II, Sparus aurata IGF-II, rainbow trout IGF-II, human IGF-II, rat IGF-II, mouse IGF-II, sheep IGF-II, and chicken IGF-II. Sequences start at the first methionine peptide amino acid residue. The IGF-II prepropeptide is divided into the signal peptide, and the B, C, A, D and E domain. A dot (.) represents a gap/deletion.

DESCRIPTION OF THE PREFERRED EMBODIMENTS

Figure 3:
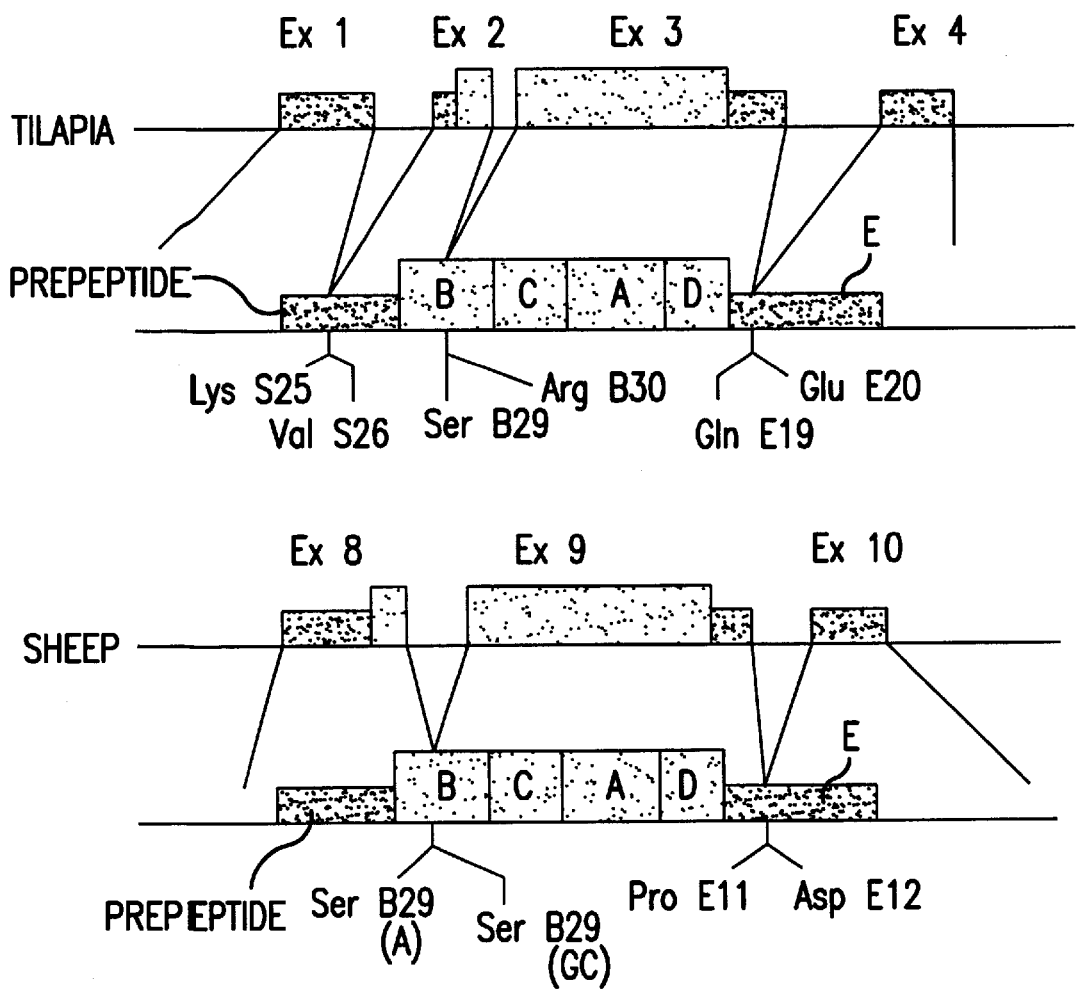
FIG. 3 is a comparison of sheep coding region structure and the organization of the tilapia IGF-II coding region. Exons are shown by boxes, and introns and flanking sequence are shown by thin lines. At the bottom of each structure are the relative locations of the exon and intron boundaries.

The following embodiments are directed to (1) the findings of fish IGF-II CDNA, (2) the expression of fish recombinant IGF-II polypeptide, and (3) the biological activity of fish recombinant IGF-II polypeptides.

EMBODIMENT 1: Findings of Fish IGF-II cDNA

One of the objectives of the present invention is the finding of the coding region of fish IGF-II cDNA. This finding is exemplified by the following procedures, which are directed to, but not limited to, the species of tilapia:

EXAMPLE 1
Isolation of Fish IGF-II cDNA Clones.

Fish IGF-II CDNA clones were selected by a plaque hybridization method using the S domain to E domain of *Acanthopagrus schlegeli* IGF-I cDNA (which was amplified by PCR method) as a probe. A detailed plaque hybridization method using tilapia (hybrid) brain CDNA library as an example is described as follows (Please note that the method described below also applies to the selection of cDNA from the cDNA library of other fish species, e.g., salmon and carp):

First, the S domain to E domain region of *Acanthopagrus schlegeli* IGF-I cDNA was amplified by PCR method. This PCR product, which was approximately 551 bp in length, was further purified by electroelution and used as a hybridization probe.

Second, approximately 1 million recombinant bacteriophages, which were from the tilapia (hybrid) brain CDNA library, were seeded on 12 LB plates. These seeded bacteriophages were then transferred to nylon membranes.

Third, the PCR hybridization probe was then hybridized with said recombinant bacteriophages that sat on the nylon membranes. After a denaturing, renaturing and cross-linking procedure, the hybrids were incubated in a hybridization buffer [containing SDS (7 g/100 ml), 0.5 M EDTA (pH 8.0) (100 µl/100 ml), 50% PEG8000 (20 ml/100 ml), 40% formamide (40 ml/100 ml)] at 37° C. for 16 hrs.

Finally, positive plaques were selected by washing filters in 2×SSC, 0.1% SDS; 0.5×SSC, 0.1% SDS; 0.1×SSC, 0.1% SDS at room temperature, 37° C., and 40° C.

In addition to the above procedures, in vivo excision of the pBluescript phagemid from the Uni-ZAP vector was also used to facilitate recombinant DNA preparation and characterization.

As a result of this plaque hybridization method, a positive tilapia IGF-II cDNA clone was obtained. This positive clone contained pBluescript double-stranded phagemids with the cloned DNA insert, was further used for large-scale plasmid preparation.

EXAMPE 2
Isolation of Fish IGF-II Genomic Clones.

The fish IGF-II genomic clones were isolated by screening approximately 1 million recombinant bacteriophages from the a fish genomic library with $^{32}$P-labeled fish IGF-II cDNA fragments (the fish genomic DNA library was constructed in phage charon 40 cloning vector) in hybridization buffer (supra) at 42° C. for 16 hrs. The positive plaques were purified and DNA restriction mapping of these positive plaques was further conducted by southern blotting using $^{32}$P-labeled tilapia IGF-II CDNA probes.

EXAMPLE 3
Nucleotide Sequence Analysis.

To analyze the nucleotide sequence of fish IGF-II cDNA, the entire CDNA from a fish species (e.g., tilapia, salmon, and carp) was first digested with PstI restriction enzyme, and then subcloned into pUC18 and transformed into JM109, which was then sequenced by the Sanger dideoxy chain termination method and sequenase kit (USB, version 2.0). To analyze the nucleotide sequence of fish IGF-II genomic DNA, the IGF-II phage DNAs were digested with SacI restriction enzyme, then subcloned into the pBluescript vector and transformed into XL1 Blue *E. coli* host cells.

Finally, a QIAGEN plasmid extraction kit was used to extract DNA and one strand of DNA was sequenced by an ABI autosequencer. The nucleic acid sequences were compared with all published sequences on the Genetics Computer Group computer program.

RESULTS

FIG. 1 shows the nucleotide sequence of tilapia (hybrid) IGF-II cDNA and the predicted amino acid sequence of the hormone. The 5'UTR sequence contained a total of 76 nucleotides in length. The 3'UTR sequence contained a total of 1,247 nucleotides in length. The coding region had a total of 645 nucleotides in length.

Tilapia IGF-II polypeptide contained the following peptides:

(1) A signal or leader peptide of 47 amino acid residues (1–47). This signal peptide was encoded by a cDNA having the sequence of SEQ ID NO:2:

5'ATGGAAACCCAGCAAAGATACGGACATCACTCACTTTGCCACCAGTGCCGGAGAACGC

AGAACAGCAGAATGAAGGTCCAGAGGATGTCTTCGACGAGTCGGGCGCTGCTCTTTGCAC

TGGCCCTGACGCTCTACGTAGTG.

The signal peptide had the amino acid sequence of SEQ ID NO:5: Met-Glu-Thr-Gln-Gln-Arg-Tyr-Gly-His-His-Ser-Leu-Cys-His-Thr-Cys-Arg-Arg-Thr-Gln-Asn-Ser-Arg-Met- Lys-Val-Gln-Arg-Met-Ser-Ser-Thr-Ser-Arg-Ala-Leu-Leu-Phe-Ala-Leu-Ala-Leu-Thr-Leu-Tyr-Val-Val.

(2) A B to D domain polypeptide [i.e., the IGF-II mature peptide, in which B domain peptide had 32 amino acid residues (48–79), C domain peptide had 11 amino acid residues (80–90), A domain peptide had 21 amino acid residues (91–111), and D domain peptide had 6 amino acid residues (112–117), respectively]. This IGF-II mature peptide was encoded by a cDNA having the sequence of SEQ ID NO:1:

5'GAAATGGCCTCGGCGGAGACGCTGTGTGGGGAGAACTGGTGGATGCGCTGCAGTTTG

TCTGTGAAGACAGAGGCTTTTATTTCAGTAGGCCAACCAGCAGGGGTAACAACCGACGCC

CCCAGACCCGTGGGATCGTAGAGAGTGTTGTTTCCGTAGCTGTGACCTCAACCTACTGGA

GCAGTACTGTGCAAACCTGCCAAGTCCGAAAG.

The mature peptide (70 amino acids in length) had the amino acid sequence of SEQ ID NO:4: Glu-Met-Ala-Ser-Ala-Glu-Thr-Leu-Cys-Gly-Gly-Glu-Leu-Val-Asp-Ala-Leu-Gln-Phe-Val-Cys-Glu-Asp-Arg-Gly-Phe-Tyr-Phe-Ser-Arg-Pro-Thr-Ser-Arg-Gly-Asn-Asn-Arg-Arg-Pro-Gln-Thr-Arg-Gly-Ile-Val-Glu-Glu-Cys-Cys-Phe-Arg-Ser-Cys-Asp-Leu-Asn-Leu-Leu-Glu-Gln-Tyr-Cys-Ala-Lys-Pro-Ala-Lys-Ser-Glu.

(3) An E domain peptide of 98 amino acid residues (118–216).
This E peptide was encoded by a cDNA having the sequence of SEQ ID NO:3:

5'AGGGGACGTGTCAGCCACCTCTCTACAGGTCATACCGGTGATGCCCGCACTAAAACAGG

AAGTTCCGAAGAAGCAACATGTGACCGTGAAGTATTCCAAATACGAGGTGTGGCAGAGGA

AGGCGGCCCAGCGGCTCCGGAGGGGTGTCCCCGCCATTCTGAGGGCCAGAAAGTATAAGA

GGCACGCGGAGAAGATTAAAGCCAAGGAGCAGGCTATCTTCCACAGGCCCCTGATCAGCC

TTCCTAGCAAGCTGCCTCCCGTGTTACTCACCACGGACAACTTTGTCAGTCACAAA.

The E peptide had the amino acid sequence of SEQ ID NO:6:

Arg Asp Va; Ser Ala Thr Ser Leu Gln Val Ile Pro Val Met Pro

Ala Leu Lys Gln Glu Val Pro Lys Lys Gln His Val Thr Val Lys

Tyr Ser Lys Tyr Gln Val Trp Gln Arg Lys Ala Ala Gln Arg Leu

Arg Arg Gly Val Pro Ala Ile Leu Arg Ala Arg Lys Tyr Lys Arg

His Ala Glu Lys Ile Lys Ala Lys Glu Gln Ala Ile Phe His Arg

Pro Leu Ile Ser Leu Pro Ser Lys Leu Pro Pro Val Leu Leu Thr

Thr Asp Asn Phe Val Ser His Lys

FIG. 2 shows the comparative studies of IGF-II amino acid sequences among different species of animals. Among fish species, the IGF-II mature polypeptide between tilapia and rainbow trout IGF-II (B to D domains) shared a 95.7% similarity and a 92.9% identity. In addition, as comparing the preproproteins (S to E domains) between tilapia and rainbow trout IGF-II, the similarity was 90.7% and the identity was 81.8%.

However, the tilapia IGF-II mature polypeptide, as compared to the mature proteins in chicken, human, rat, mouse, and sheep, only shared 83.1%, 79.1%, 80.6%, 83.6%, and 80.6% in similarities, and 78.5%, 77.6%, 79.1%, 79.1%, and 79.1% in identities, respectively. Also, in comparison with the mammalian IGF-II mature peptides, the tilapia IGF-II mature peptide had a 3-codon insertion at the C domain, and a 2-codon deletion at the B domain. In particular, the tilapia IGF-II at position B22 was a Glu, contrasting to a Ser in rat and mouse and a Gly in humans. The real mechanism with regard to the change of Glu (in fish) to ser (in mouse or rat) to gly (in humans) at B22 is unknown.

FIG. 2 also shows that the tilapia IGF-II mature polypeptide had 5 amino acids differences from those of the other two published fish species (i.e., Sparus aurata and rainbow trout): they were: (1) at B2 (in tilapia: Met; in S. aurata and rainbow trout: Val); (2) at C3 (in tilapia and S. aurata: gly; in rainbow trout: Ser); (3) at C5 (in tilapia and S. aurata: Asn; in rainbow trout: Ser); (4) at C8 (in tilapia and S. aurata: Pro; in rainbow trout: Ser); and (5) at C10 (in tilapia: Thr; in S. aurata and rainbow trout: Asn).

FIG. 3 shows the genomic DNA sequences between tilapia and sheep. The genomic DNA sequences of the tilapia coding region were divided into 4 exons (i.e., exons 1–4) and spanned approximately 12.9 kb, contrasting to mammalian IGF-II genes which were comprised of 3 exons. The coding region of tilapia IGF-II gene predicts a prepropeptide of 215 amino acids, including a 47 amino acid signal peptide, a 70 amino acid mature peptide, and a 98 amino acid E peptide. The predicted amino acid sequences of tilapia IGF-II, were consistent to those determined by cDNA sequence data.

Exon 1 of the Tilapia IGF-II gene was from 5'UTR (as compared to the cDNA sequence) to part of the signal peptide (up to S25); exon 2 was from the rest of the signal peptide (S26) to B domain (up to B28); exon 3 was from C domain (C1) to E domain (up to E20); and exon 4 was from E domain to part of the 3'UTR. In other words, exon 1 encoded 25 amino acids, exon 2 encoded 51 amino acids, exon 3 encoded 60 amino acids, and exon 4 encoded 80 amino acids.

Between exons 1 and 2, there was an intron of about 0.8 kb; between exons 2 and 3, there was an intron of about 2.8 kb; and between exons 3 and 4, there was an intron of about 1.3 kb. The sequences of the exon-intron junctions were conformed to the GT-AG rule. The genomic structure of the tilapia IGF-II coding region, which was highly conserved among different fish species, showed great variation as compared with the mammalian IGF-II gene organization, suggesting that a divergence of IGF-II gene structure might have taken place during the evolution of vertebrates.

EMBODIMENT 2: Expression of Fish Recombinant IGF-II Polypeptide

A fish IGF-II cDNA, which has been identified and isolated from the plaque hybridization method as demonstrated in Example 1, is capable of being expressed in various cells to produce a biologically active IGF-II polypeptide. The establishment of a gene expression system for the production of fish recombinant IGF-II polypeptide is exemplified by the following procedures using tilapia as a model (please note that the same procedures can be used to construct a recombinant IGF-II expression vector where the cDNA is derived from other fish species, e.g., salmon and carp):

EXAMPLE 4

Construction of Recombinant IGF-II Expression Vector

A fish IGF-II CDNA containing B to D domains, was amplified by PCR using the following two primers:

```
Primer 1: 5'-CGGAATTCATATGGAAATGGCCTCGGGCGGAGACGC;

Primer 2: 5'-CGGAATTCCTCATTCGGACTTGGCAGGTTTGGCAC.
```

These two primers each contained an EcoRI site. The ATG initiation codon was designed in the head of the fish IGF-II B domain, and the stop codon was connected after the final sequence of the fish IGF-II D domain.

There are four kinds of cells that demonstrate expression capability for fish IGF-II cDNA, they are: *E. coli*, yeast, baculovirus, and fish cells. For cloning and expressing fish IGF-II in *E. coli*, the recombinant IGF-II cDNA construct was constructed with a glutathione-s-transferase (GST) gene fusion system (Pharmacia Biotech Co.) of expression vector (pGEX-2T). Both of *E. coli* K12 strains (such as HMS174, HB101, JM109, DH5α and NovaBlue), and B strain (such as BL21, BL21(DE3), B834, B834(DE3)) can be used for the expression and BL21(DE3) is the preferable choice in obtaining the highest quality and quantity of IGF-II polypeptide. For cloning and expressing fish IGF-II in yeast, a *Pichia pastoris* (a methylotrophic yeast) expression kit (Invitrogen Co.) can be used. The Invitrogen *Pichia pastoris* expression systems contain three different kits (namely, the Original Pichia Expression kit, the EasySelect Pichia Expression Kit, and the Multi-Copy Pichia Expression Vectors), each contains a set of vectors, *Pichia pastoris* strains, and reagents for transformation. In addition, pYES2 vector can be used as an expression vector for *S. cerevisiae* strain INVSc1 of yeast.

For cloning and expressing fish IGF-II in baculovirus, a MaxBac 2.0 Kit (Invitrogen Co.) can be used. This kit contains baculovirus transfer vectors (pBlueBac4.5, pBlueBacHis2, pBlueBac4.5/CAT [positive control], pVL1392, and pVL1393) and *Spodoptera frugiperda* (Sf9) insect cells. Additionally, *Spodoptera frugiperda* ovarian cells (Sf21) cells and High Five cells (BTI-TN-5B1-4) are also recommended for expressing IGF-II. In case that High Five cells are used, pMelBac is the ideal vector for IGF-II gene expression.

For cloning and expressing fish IGF-II in salmon, the IGF-II cDNA construct can be transferred to an expression vector p91023(B) under the control of the adenovirus major late promoter. This expression vector can then be transfected into chinook salmon embryo CHSE-214 cells. The same cloning method also applies to the transfection of IGF-II cDNA construct into tilapia ovary cell line (TO-2 cells).

EXAMPLE 5

Purification of Fish Recombinant IGF-II Polypeptide in *E. coli*

A fish IGF-II recombinant protein can be purified by the following procedures using an *E. coli* cell expression system:

(1) inoculating a single colony of BL21(DE3) *E. coil* cells containing a recombinant PGEX-IGF-II plasmid in 100 ml 2×YTA medium (tryptone 16 g/L, yeast extract 10 g/L, NaCl 5 g/L, and ampicillin 100 μg/mL) and incubating said cells at 37° C. for 10 hrs with shaking;

(2) transferring 5 ml of the culture into 500 mL 2×YTA medium and incubated at 37° C. with shaking until the absorbance at 600 nm was 1.1;

(3) adding 0.1M isopropyl-thio-D-galactoside to the culture medium and incubating the culture at 25° C. for 3 hrs with shaking;

(4) centrifuging the culture at 7700×g for 10 minutes at 4° C. and resuspending the cells by adding 50 μl of ice-cold 1×PBS per milliliter of culture;

(5) disrupting the cells by sonication and adding 1% triton X-100 (final concentration) to the sonicates;

(6) centrifuging the lysed cells at 12,000×g for 10 minutes at 4° C. and passing the supernatant through a 0.45 μm filter;

(7) aspirating the filtrate into a column (Pharmacia Biotech Co.) and washing the column with 1×PBS, followed by a thrombin solution at 25° C. for 16 hrs;

(8) collecting the reaction mixture which contained the IGF-II protein;

(9) running the reaction mixture on a 15% SDS-PAGE gel to separate the recombinant IGF-II polypeptides from GST protein.

The gel was transferred to a PVDF membrane for further amino acid sequence analysis. Alternatively, the recombinant IGF-II polypeptides on the gel were blotted onto a Hybond™ ECL™ nitrocellulose membrane (Amersham Life Science Co.) and detected by anti-IGF monoclonal antibodies.

RESULTS

To express fish recombinant IGF-II polypeptides in BL21 (DE3) *E. coli* cells containing recombinant IGF-II plasmids, the cells were induced with 0.1 mM IPTG and grown for 3 hrs at 22° C. The total proteins extracted from the above method showed a clear band of 36 kDa (after 30 to 180 minutes of IPTG induction) on the SDS-PAGE gel. This 36 kDa contained the mature IGF-II polypeptide which was bound to a fusion protein GST produced during the IPTG induction. When this 36 kDa protein was further digested with thrombin, a 7 kDa single band protein was produced. ECL western blotting demonstrated that this 7 kDa protein interacted with monoclonal anti-IGF antibody. Amino acid sequence analysis indicated that this 7 kDa protein had additional 7 amino acids before the predicated IGF-II mature polypeptides. Of these 7 additional amino acids, 6 were from the pGEX-2T multiclonal site DNA sequence and the remaining one was an ATG start codon.

EMBODIMENT 3: Biological Activity of Fish Recombinant IGF-II Polypeptides

The biological activity of fish recombinant IGF-II polypeptides were detected both in vitro and in vivo using tilapia ovary cell line TO-2 and juvenile tilapia as examples.

EXAMPLE 6

Bioactivity of Tilapia Recombinant IGF-II Polypeptides in Tilaria TO-2 Cell Line The bioactivity of tilapia recombinant IGF-II polypeptide was measured in vitro using tilapia ovary cell line (TO-2) by the following procedures [TO-2 cell line was established from ovaries of healthy adult tilapia hybrids (*Tilapia mossambica* X *Tilapia nilotica*)]:

(1) seeding TO-2 cells ($3 \times 10^4$ cells/well) in 24 well-plates containing MEM/F12 medium supplemented with 10% BSA for 24 hrs (serum-free incubation);

(2) further incubating said cells with or without various amounts of IGF-II (0–120 nM) for 18 hrs;

(3) pulse-labelling said cells with [$^3$H] thymidine (2 $\mu$Ci/mL) for 2 hrs at 25° C.;

(4) adding 0.5 mL of 0.3N NaOH and after standing for 5 minutes, transferring the cell mixture to a scintillation vial to which 5 ml of aquasol was added.

RESULTS

Figure 4:
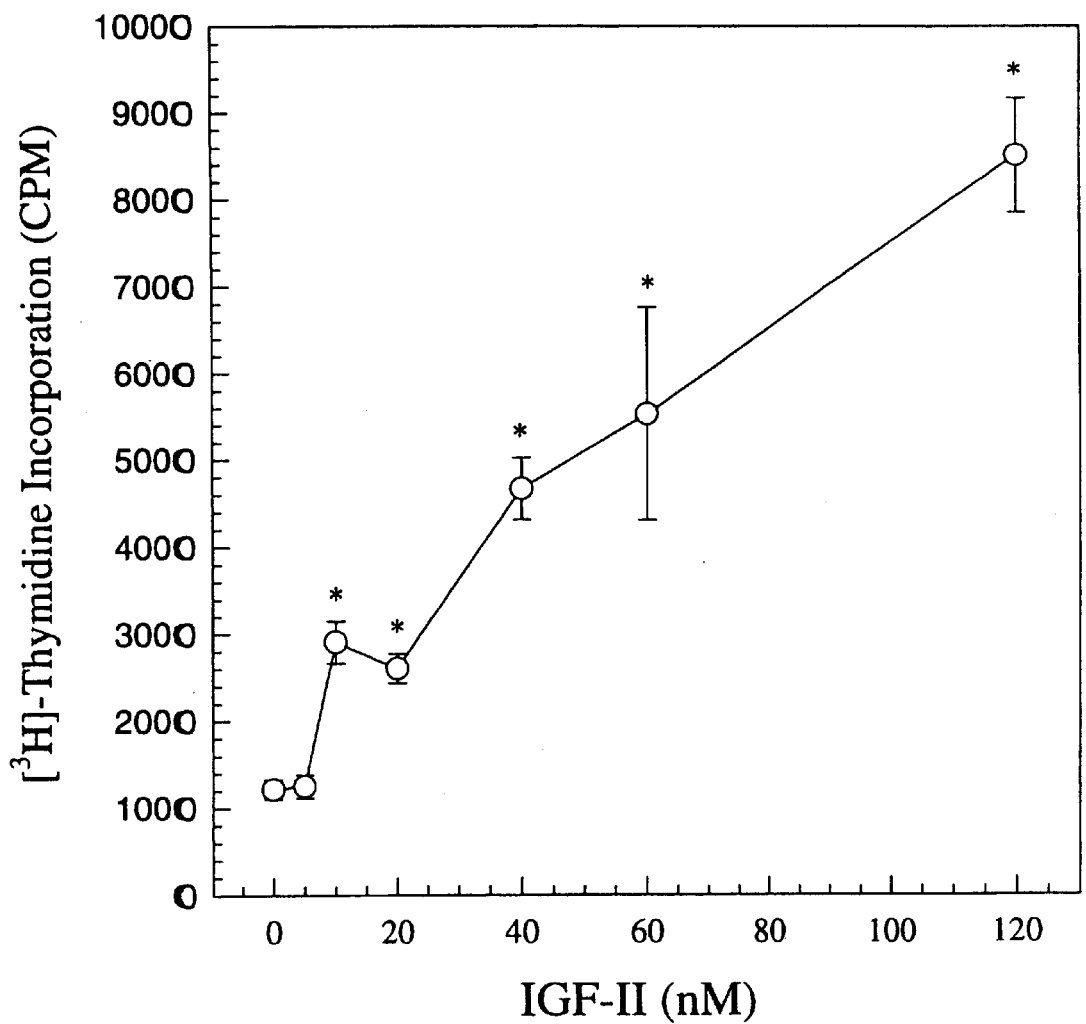
FIG. 4 shows the in vitro stimulatory effects of recombinant tilapia IGF-II polypeptide in tilapia ovary cells (TO-2 cell line).

The result of this experiment is shown in FIG. 4. The test concentrations were between 0 and 120 nM/mL of tilapia recombinant IGF-II proteins. FIG. 4 shows that [$^3$H] incorporation increased proportional to the increase in IGF-II proteins (ANOVA; F=4.46; df.=6.14; P<0.05), suggesting that the stimulatory effect of the tilapia recombinant IGF-II protein is dose-dependent.

EXAMPLE 7

Effects of Tilaria Recombinant IGFs on Fish Growth

To identify whether tilapia recombinant IGF-II produced by *E. coli* was biologically active, tilapia with an average of 1.30±0.31 g of body weight and 4.51±0.38 cm of total length were randomly selected. All fish were maintained in freshwater and fed once daily with meal particle (crude protein, 32%; crude lipid, 5%; fiber, 2%; moisture, 9%; Amazon Feed Corp., Taiwan) at a ratio of 5% of total wet weight throughout the experiments. All fish were maintained at room temperature and a 12-hr light, 12-hr dark cycle.

One group of tilapia (20 tilapia per group) was given IGF-II by intraperitoneal injection once a week for a duration of 10 weeks as the experimental group. Another group of tilapia was given no IGF-II injection as control. The amount of IGF-II given was in the concentrations of 0.1, 0.5. 1, and 2 $\mu$g per g of body weight per fish. The wet weight and total length of fish were measured once every 2 weeks. Percentages (%) of Body weight gain and body length gain were calculated as (WT-wt) X wt$^{-1}$×100; where wt and WT represented initial and final mean wet weight (body length gain was measured as the body length distance from the tip of the lower jaw to the fork (cm)), respectively. All data were analyzed by 1-way analysis of variance.

RESULTS

To determine whether the tilapia recombinant IGF-II expressed in *E. coli* was biologically active, an experiment which involved the injection of the purified IGF-II polypeptides from *E. coli* cells into juvenile tilapia was conducted and the growth of the fish, as measured by % weight gain and % length gain, was carefully monitored.

The data show that higher doses of IGF-II polypeptides injection produced greater growth rates in fish, except for 0.1 $\mu$g of IGF-II injection which showed insignificant weight gain as compared to the controls. Similarly, the 0.1 $\mu$g of IGF-II injection did not produce a conspicuous body length gain.

At the end of the 10 weeks treatment, % of weight gain in each group of tilapia obtaining various amounts of IGF-II injection was as follows:

(1) 2 $\mu$g of IGF-II: 259%; (2) 1 $\mu$g of IGF-II: 242%;

(3) 0.5 $\mu$g of IGF-II: 231%; (4) 0.1 $\mu$g of IGF-II: 200%;

(5) Control: 153%. The results indicated that the highest dose of IGF-II injection (i.e., 2 $\mu$g of IGF-II) showed the most % weight gain in tilapia.

The actual wet weight and length (measured as MEAN±SE) in each of the tilapia groups were as follows:

(A) Wet Weight:

(1) 2 $\mu$g of IGF-II: 4.67±1.50 g;

(2) 1 $\mu$g of IGF-II: 4.45±1.85 g;

(3) 0.5 $\mu$g of IGF-II: 4.33±1.30 g;

(4) 0.1 $\mu$g of IGF-II: 3.90±0.81 g;

(5) Control: 3.41±0.72 g.

(B) Total Length:

(1) 2 $\mu$g of IGF-II: 6.78±0.73 cm;

(2) 1 $\mu$g of IGF-II: 6.63±0.76 cm;

(3) 0.5 $\mu$g of IGF-II: 6.59±0.66 cm;

(4) 0.1 $\mu$g of IGF-II: 5.88±0.47 cm;

(5) Control: 5.81±0.41 cm.

We claim:

1. An isolated and purified DNA molecule, wherein the DNA molecule comprises the nucleic acid sequence of SEQ ID NO:1.

2. The isolated and purified DNA molecule of claim 1, wherein the DNA molecule encodes the amino acid sequence of SEQ ID NO:4.

3. A vector comprising the DNA molecule of claim 1.

4. A host cell comprising the vector of claim 3, wherein the host cell is *Escherichia coli*.

5. A method of producing a protein comprising the amino acid sequence of SEQ ID NO:4, said method comprising:

expressing the host cell of claim 4 under conditions suitable for expression of the isolated and purified DNA.

6. A host cell comprising the vector of claim 3, wherein the host cell is a yeast cell.

7. A method of producing a protein comprising the amino acid sequence of SEQ ID NO:4, said method comprising:

expressing the host cell of claim 6 under conditions suitable for expression of the isolated and purified DNA.

8. A host cell comprising the vector of claim 3, wherein the host cell is baculovirus.

9. A method of producing a protein comprising the amino acid sequence of SEQ ID NO:4, said method comprising:

expressing the host cell of claim 8 under conditions suitable for expression of the isolated and purified DNA.

10. A host cell comprising the vector of claim 3, wherein the host cell is a fish cell.

11. The host cell according to claim 10, wherein the fish cell is salmon embryo cell.

12. The host cell according to claim 10, wherein the fish cell is tilapia ovary cell.

13. A method of producing a protein comprising the amino acid sequence of SEQ ID NO:4, said method comprising:

expressing the host cell of claim 10 under conditions suitable for expression of the isolated and purified DNA.

14. An isolated and purified DNA molecule, wherein the DNA molecule comprises the nucleic acid sequence of SEQ ID NO:2.

15. The isolated and purified DNA molecule of claim 14, wherein the DNA molecule encodes the amino acid sequence of SEQ ID NO:5.

16. An isolated and purified DNA molecule, wherein the DNA molecule comprises the nucleic acid sequence of SEQ ID NO:3.

17. The isolated and purified DNA molecule, wherein the DNA molecule encodes the amino acid sequence of SEQ ID NO:6.

* * * * *